(12) United States Patent
Upasani et al.

(10) Patent No.: US 9,701,814 B2
(45) Date of Patent: Jul. 11, 2017

(54) POLYMERIC COMPOSITION AND A METHOD FOR PREPARATION THEREOF

(71) Applicant: RELIANCE INDUSTRIES LIMITED, Mumbai, Maharashtra (IN)

(72) Inventors: Prasad Suresh Upasani, Maharashtra (IN); Anil Krishna Kelkar, Maharashtra (IN); Veedu Sreekumar Thaliyil, Kerala (IN); Uday Shankar Agarwal, Maharashtra (IN)

(73) Assignee: Reliance Industries Limited, Mumbai, Maharashtra (IN)

( * ) Notice: Subject to any disclaimer, the term of this patent is extended or adjusted under 35 U.S.C. 154(b) by 0 days.

(21) Appl. No.: 14/759,746

(22) PCT Filed: Dec. 31, 2013

(86) PCT No.: PCT/IN2013/000820
§ 371 (c)(1),
(2) Date: Jul. 8, 2015

(87) PCT Pub. No.: WO2014/108914
PCT Pub. Date: Jul. 17, 2014

(65) Prior Publication Data
US 2015/0353709 A1  Dec. 10, 2015

(30) Foreign Application Priority Data
Jan. 8, 2013  (IN) .............................. 61/MUM/2013

(51) Int. Cl.
| A01N 53/00 | (2006.01) |
| C08J 5/00 | (2006.01) |
| C08K 5/315 | (2006.01) |
| A01N 25/10 | (2006.01) |
| A01N 25/34 | (2006.01) |

(52) U.S. Cl.
CPC .............. *C08K 5/315* (2013.01); *A01N 25/10* (2013.01); *A01N 25/34* (2013.01); *C08J 5/00* (2013.01); *C08J 2323/06* (2013.01); *C08J 2339/06* (2013.01)

(58) Field of Classification Search
None
See application file for complete search history.

(56) References Cited

U.S. PATENT DOCUMENTS

| 3,755,064 A * | 8/1973 | Maierson ............... A01N 25/10 264/182 |
| 4,116,909 A * | 9/1978 | Muller ..................... C08J 3/226 106/419 |
| 4,354,004 A * | 10/1982 | Hughes ................... C08L 23/20 525/240 |
| 4,684,576 A * | 8/1987 | Tabor ....................... B32B 7/12 428/441 |
| 7,311,216 B2 * | 12/2007 | Donnelly ................ B29C 65/18 220/1.5 |
| 2002/0147298 A1 * | 10/2002 | Sun ........................ C08G 69/44 528/310 |
| 2002/0165302 A1 * | 11/2002 | Lamba ..................... C08K 9/04 524/254 |
| 2005/0272336 A1 * | 12/2005 | Chang .................. C08K 5/0058 442/123 |
| 2007/0049497 A1 | 3/2007 | Parker et al. |
| 2009/0041820 A1 | 2/2009 | Wu et al. |
| 2011/0165213 A1 * | 7/2011 | Vestergaard Frandsen ............... A01N 53/00 424/409 |
| 2012/0172214 A1 * | 7/2012 | Thomas ................. B01J 20/267 502/402 |

FOREIGN PATENT DOCUMENTS

| AU | 2002100853 A4 * | 6/2003 |
| EP | 2 601 837 A1 | 6/2013 |
| JP | 2000-044412 A | 2/2000 |
| WO | 99/09823 A1 | 3/1999 |
| WO | 2012/085550 A2 | 6/2012 |

OTHER PUBLICATIONS

Preparation and Characterization of LDPE and PP—Wood Fiber Composites, Tasdemir et al., Journal of Applied Polymer Science, vol. 112, 3095-3102, (2009).*
International Search Report of PCT/IN2013/000820, mailed Apr. 16, 2014.

* cited by examiner

*Primary Examiner* — Peter A Salamon
(74) *Attorney, Agent, or Firm* — Collard & Roe, P.C.

(57) ABSTRACT

The present disclosure relates to a tablet comprising at least one property modifying agent adapted to modify at least one property of a melt processable polymer and at least one processing aid having softening temperature lower than or equal to the melt processing temperature of the melt processable polymer.

11 Claims, No Drawings

POLYMERIC COMPOSITION AND A METHOD FOR PREPARATION THEREOF

CROSS REFERENCE TO RELATED APPLICATIONS

This application is the National Stage of PCT/IN2013/000820 filed on Dec. 31, 2013, which claims priority under 35 U.S.C. §119 of Indian Application No. 61/MUM/2013 filed on Jan. 8, 2013, the disclosures of which are incorporated by reference. The international application under PCT article 21(2) was published in English.

FIELD OF THE DISCLOSURE

The present disclosure relates to a polymeric composition. The present disclosure particularly relates to a method for incorporating property modifying agents into the polymeric composition.

BACKGROUND

A polymer is a macromolecule composed of repeating structural units of monomers. Wide ranges of properties of polymers are achieved through selection of a base polymer and a property modifying agent. Various types of polymer property modifying agents are known and they belong to different categories depending upon their chemical structure or chemical/physical properties or the manner in which they modify the polymers. Examples of such broader categories of the polymer property modifying agents include surfactants to stabilize emulsion polymers, chain transfer agents and other polymerization modifiers to control molecular weight, plasticizers to increase flexibility, stabilizers to prevent polymer degradation, and cross-linkers used to modify polymer networks and the like. Apart from the above mentioned agents, the property modifying agents also include various substances that impart specific functional properties to the end product. Examples of such substances include antimicrobial agents, mosquito repellents, perfumes, an emulsifier, coloring dye, and the like.

Conventionally, property modifying agents are added in a polymer through master-batch route, wherein the masterbatch is a concentrate prepared by melt compounding of property modifying agents and the polymer. However, some of thermally sensitive property modifying agents degrades during melt compounding. Further, the fumes resulting from these thermally sensitive agents during melt-compounding process are toxic and they pose serious hazards to human and animal health as well as to the environment.

There is, therefore, felt a need for a method for incorporating the property modifying agents in the polymer during the manufacturing of the polymeric product from the polymer which obviates the method step of melt-compounding thereby avoiding the thermal degradation of property modifying agents. Also, there exists a need for a method that allows incorporation of small amount of property modifying agents in the polymer during the manufacturing of the polymeric product from the polymer.

OBJECTS

Some of the objects of the present disclosure are described herein below:

It is an object of the present disclosure to ameliorate one or more problems of the prior art or to at least provide a useful alternative.

It is another object of the present disclosure to provide a formulation containing a property modifying agent which can be used to impart specific properties to the polymer.

It is still another object of the present disclosure to provide a simple and economic method for incorporation of the formulation into a polymer to reduce degradation of the property modifying agent.

It is yet another object of the present disclosure to provide a property modified bi-component filament.

It is yet another object of the present disclosure to provide a woven or non-woven fabric made from the property modified bi-component filament.

Other objects and advantages of the present disclosure will be more apparent from the following description.

DEFINITIONS

As used in the present specification, the following words and phrases are generally intended to have the meanings as set forth below, except to the extent that the context in which they are used to indicate otherwise.

The term 'Property modifying agent' in the present disclosure is used to define materials which can be used to make and modify polymer characteristics.

The term 'thermally sensitive property modifying agent' is used to define an agent whose noticeable and/or unacceptable degradation or loss due to evaporation or change in physical characteristics initiates at or before the melt processing temperature of the final melt processable polymer in which it is to be incorporated.

The term 'article' in the context of the present disclosure has been used in a broadest possible sense and it includes fibers, mono filaments, spun filaments, staple filaments, bi-component filaments, multi-component filaments, monocomponent yarns, bi-component yarns, multicomponent yarns, fabrics, uni-layer films, bi-layer films, multi-layer films, packaging films, printing labels, sheets, molded articles, pipes, tubes, bottles, plastic bags, screens, cables and oriented products.

The term 'yarn' in the context of the present disclosure has been used in a broadest possible sense and it includes fully drawn yarn (FDY), partially oriented yarn (POY), textured yarn, low oriented yarn (LOY), spun drawn yarn (SDY), IDY (Industrial yarn), fiber fill applications and staple fiber.

The term 'tablet' means a formulation in a solid form which includes but is not limited to tablet, pellet, granules and caplet.

The term 'processing aid' in the context of the present disclosure has been used in a broadest possible sense and it includes any substance assisting in making of a tablet such as carrier, binders, diluents, lubricants, glidants, dispersing agents, disintegrants and the like.

The term 'carrier' means a material that gets mixed in the final melt processable polymer and also appropriately dilutes the concentration of the property modifying agent in the tablet as needed.

The term "binder" means material that helps provide physical integrity to the tablet and avoid attrition.

The term 'degradation temperature' in the context of the present disclosure has been used in a broadest possible sense and it includes temperature at which property modifying agent evaporates, degrades or denatures.

The term 'Synergist' in the context of the present disclosure has been used in a broadest possible sense and it includes natural or synthetic chemicals or compounds which increase the efficacy or bio-efficacy or activity of the other compound/s.

SUMMARY

In accordance with one aspect of the present disclosure there is provided a tablet comprising at least one property modifying agent adapted to modify at least one property of a melt processable polymer and at least one processing aid having a softening temperature lower than or equal to a melt processing temperature of the melt processable polymer; wherein the amount of the processing aid is at least 0.005% with respect to the total mass of the tablet and the melt processing temperature of the melt processable polymer is higher than or equal to the initial degradation temperature of the property modifying agent.

Typically, the property modifying agent is at least one selected from the group consisting of surfactants, polymerization modifiers, plasticizers, stabilizers, colorants, toners, antimicrobial agents, insect repellants, insecticides, catalysts, initiators, chain extenders, and cross linkers.

Typically, the property modifying agent is at least one insect repellant selected from the group consisting of deltamethrin, permethrin, fenvalerate, cypermethrin, bifenthrin, resmethrin, sumethrin and n-octyl bicycloheptene dicarboximide.

Typically, the property modifying agent is deltamethrin.

Typically, the property modifying agent is at least one synergist selected from the group consisting of piperonyl butoxide and n-octyl bicycloheptene dicarboximide.

Typically, the property modifying agent is at least one insecticide and at least one synergist.

Typically, the processing aid is at least one selected from the group consisting of carriers, binders, lubricants, glidants, dispersing agents and disintegrants.

Typically, the melt processable polymer is at least one polymer selected from the group consisting of polyethylene terephthalate, polypropylene, polyethylene, poly methyl methacrylate, polystyrene, polycarbonate, polyamide and high density polyethylene.

Typically, the processing aid is at least one carrier selected from the group consisting of polymeric carriers, oligomeric carriers and monomeric carriers.

Typically, the processing aid comprises at least one polymeric carrier selected from the group consisting of Acrylonitrile butadiene styrene (ABS), Cellulose acetate, Cellulose, Ethyl cellulose, Fluoroplastics (PTFE) Cyclic Olefin Copolymer (COC), Ethylene-Vinyl Acetate (EVA), acrylic/PVC alloy, Ethylene vinyl alcohol (EVOH), Liquid Crystal Polymer (LCP), Polyoxymethylene (POM or Acetal), Polyacrylates (Acrylic), Polyacrylonitrile (PAN or Acrylonitrile), Polyaryletherketone (PAEK or Ketone), Polybutylene terephthalate (PBT), Polycaprolactone (PCL), Polychlorotrifluoroethylene (PCTFE), Polyethylene terephthalate (PET), Polycyclohexylenedimethylene terephthalate (PCT), Polyhydroxyalkanoates (PHAs), Polyketone (PK) Polyester, Polyethylene (PE), Polyetheretherketone (PEEK), Polyetherketoneketone (PEKK), Polyethersulfone (PES)/Polysulfone, Chlorinated Polyethylene (CPE), Polylactic acid (PLA), Polymethylpentene (PMP), Polyphenylene oxide (PPO), Polyphenylene sulfide (PPS), Polypropylene (PP), Polystyrene (PS), Polysulfone (PSU), Polytrimethylene terephthalate (PTT), Polyvinyl acetate (PVAc), Polyvinyl alcohol (PVA), Polyvinyl chloride (PVC), Polyvinylidene chloride (PVDC), High Density Polyethylene (HDPE), Low Density Polyethylene (LDPE), Polyvinyl Chloride (PVC), Polymethylmethacrylate (PMMA), p-Polycarbonate (PC), Polyaryletherketone (PAEK) and Self-reinforced polyphenylene (SRP), Polyvinylidene chloride (PVDC), Styrene-acrylonitrile (SAN), Polychlorotrifluoroethylene (PCTFE), Nylon, Teflon, Thermoplastic polyurethanes, Phenol-formaldehyde resin, Para-aramid, Polychloroprene, Polyimide, aromatic polyester, poly-p-phenylene-2,6-benzobisoxazole (PBO), Polyethylene glycol (PEG), Polyurethane (PU), Polyvinylidene fluoride (PVDF) and Ethylene methyl acrylate.

Typically, the processing aid comprises at least one oligomeric carrier selected from the group consisting of macrocyclic polycarbonates oligomer, macrocyclic polyesters oligomer, macrocyclic polyimides oligomer, macrocyclic polyetherimide oligomer, macrocyclic polyphenylene ether-polycarbonate co-oligomers, macrocyclic polyetherimide-polycarbonate co-oligomers.

Typically, the processing aid comprises at least one monomeric carrier selected from the group consisting of glucose, sorbitol, mannitol, sorbitol, fructose, maltose, xylitol, maltitol, sucrose, lactose, calcium phosphate, naphthalene, camphor, calcium stearate, magnesium stearate, sodium stearate, fumed silica, calcium carbonate, magnesium carbonate, carbon black, diatomaceous earth, magnesium silicate, calcium silicate, sodium silicate, alumina and wax.

Typically, the processing aid comprises at least one binder selected from the group consisting of Glucose, sorbitol Mannitol, Sorbitol, Fructose, Maltose, xylitol, maltitol, sucrose, lactose, starch, cellulose, microcrystalline cellulose, hydroxypropyl cellulose (HPC); Ethyl cellulose, methyl cellulose, carboxy methyl cellulose, gelatin, polyvinylpyrrolidone (PVP), polyethylene glycol (PEG), poly vinyl alcohol (PVA), Polymethycrylate, Calcium phosphate, Camphor, naphthalene, wax and water.

In accordance with another aspect of the present disclosure there is provided a method for preparation of the tablet, said method comprising mixing of at least one property modifying agent and at least one processing aid to obtain a pre-mix and subjecting said pre-mix to compression.

In accordance with another aspect of the present disclosure there is provided a method for preparation of a property modified composition containing at least one melt processable polymer; said method comprising;

a. obtaining a polymeric mix by mixing, the melt processable polymer with at least one tablet comprising at least one property modifying agent adapted to modify at least one property of the melt processable polymer and at least one processing aid having softening temperature lower than or equal to the melt processing temperature of the melt processable polymer; wherein, the melt processing temperature of the melt processable polymer is higher than or equal to the initial degradation temperature of the property modifying agent and said tablet not being heated or melted before mixing it with the melt processable polymer; and b. processing the polymeric mix in a melt processing machine under a set of melt processing conditions to obtain a property modified composition.

Typically, the mixing of at least one tablet with the melt processable polymer is carried out before melting the melt processable polymer.

Typically, the mixing of at least one tablet with the melt processable polymer is carried out after melting the melt processable polymer.

Typically, the melt processing machine is at least one selected from the group consisting of melt spinning, blow molding, extrusion blow molding, stretch blow molding, compression molding, injection molding, film casting, film extrusion, electro-spinning, injection molding, compression molding, transfer molding, extrusion molding, blow molding, dip molding, rotational molding, thermoforming, laminating, expandable bead molding, foam molding, vacuum plug assist molding, pressure plug assist, matched mold, shrink fitting, shrink wrapping, die casting, rotational molding, thermoforming, blown film extrusion, over jacketing extrusion, tubing extrusion, co-extrusion, extrusion coating and compounding.

Typically, the melt processing condition comprises melting the melt processable polymer above a temperature selected from the group consisting of the softening temperature and the melt temperature of the melt processable polymer.

Typically, the property modified composition is molten or solid or molded or in the form of chips, flakes, sheets, fibers, filaments, yarns, films and extrusions.

In accordance with yet another aspect of the present disclosure there is provided an article configured from the property modified composition.

Typically, said article comprising;
i. at least one layer of at least one melt processable polymer; and
ii. at least one tablet as claimed in claim 1, incorporated in at least one said layer.

Typically, at least one layer is a core and at least one other said layer is a sheath around said core.

Typically, said article is a bi-component filament.

Typically, the property modified composition is in the form of fibers and the article is a woven and a non-woven fabric configured from said fibers.

DETAILED DESCRIPTION

The present disclosure is directed to solve the problem associated with the loss and/or degradation and/or denaturation of the property modifying agent during the preparation of a property modified composition. This is accomplished by formulating a tablet of the property Modifying agent(s) and then incorporating it into a melt processable polymer.

One of the distinct advantages associated with the tablet of the present disclosure is that it allows the incorporation of property modifying agents in the polymer even in trace amounts.

In accordance with one aspect of the present disclosure there is provided a tablet containing one or more property modifying agents along with processing aid. The amount of the processing aid is greater than or equal to 0.005% with respect to the total mass of the tablet.

In accordance with another aspect of the present disclosure there is provided a method for preparation of the tablet. The method involves mixing of at least one property modifying agent and at least one processing aid to obtain a pre-mix and subjecting the pre-mix to a mechanical compression or compaction to obtain a tablet.

The property modifying agent used to prepare the tablet of the present disclosure are selected from surfactants, polymerization modifiers, plasticizers, stabilizers, cross-linkers, antimicrobial agents, insect repellents, insecticides catalyst, initiators, chain extenders, colorants, toners and the combinations thereof.

The aforementioned insect repellant includes but is not limited to deltamethrin, permethrin, fenvalerate, cypermethrin, bifenthrin, resmethrin, sumethrin and n-octyl bicycloheptene dicarboximide.

In one of the exemplary embodiments, the tablet contains deltamethrin as insect repellent.

In another exemplary embodiment, the tablet contains insect repellent in combination with the synergist as the property modifying agent.

The synergist includes but is not limited to piperonyl butoxide and n-octyl bicycloheptene dicarboximide.

The processing aid used to prepare the tablet of the present disclosure is classified into various categories such as carrier, binders, diluents, lubricants, glidants, dispersing agents, disintegrants and combinations thereof.

The selection of appropriate processing aid necessitates temperature conditions such as softening temperature of the processing aid should be lower than or equal to the melt processing temperature of the melt processable polymer and furthermore said softening temperature should be higher than the initial degradation temperature of the property modifying agent.

One of the processing aids used in the tablet of the present disclosure is carrier and it is further classified as monomeric carrier, oligomeric carrier and polymeric carrier.

The monomeric carrier includes glucose, sorbitol, mannitol, sorbitol, fructose, maltose, xylitol, maltitol, sucrose, lactose, calcium phosphate, naphthalene, camphor, calcium stearate, magnesium stearate, sodium stearate, fumed silica, calcium carbonate, magnesium carbonate, carbon black, diatomaceous earth, magnesium silicate, calcium silicate, sodium silicate, alumina, wax and combinations thereof.

The oligomeric carrier used in the tablet includes macrocyclic polycarbonates oligomer, macrocyclic polyesters oligomer, macrocyclic polyimides oligomer, macrocyclic polyetherimide oligomer, macrocyclic polyphenylene ether-polycarbonate co-oligomers, macrocyclic polyetherimide-polycarbonate co-oligomers and combinations thereof.

The polymeric carrier includes Acrylonitrile butadiene styrene (ABS), Cellulose, Cellulose acetate, Ethyl cellulose, Fluoroplastics (PTFE) Cyclic Olefin Copolymer (COC), Ethylene-Vinyl Acetate (EVA), acrylic/PVC alloy, Ethylene Vinyl Alcohol (EVOH), Liquid Crystal Polymer (LCP), Polyoxymethylene (POM or Acetal), Polyacrylates (Acrylic), Polyacrylonitrile (PAN or Acrylonitrile), Polyaryletherketone (PAEK or Ketone), Polybutylene terephthalate (PBT), Polycaprolactone (PCL), Polychlorotrifluoroethylene (PCTFE), Polyethylene terephthalate (PET), Polycyclohexylenedimethylene terephthalate (PCT), Polyhydroxyalkanoates (PHAs), Polyketone (PK) Polyester, Polyethylene (PE), Polyetheretherketone (PEEK), Polyetherketoneketone (PEKK), Polyethersulfone (PES)/Polysulfone, Chlorinated Polyethylene (CPE), Polylactic acid (PLA), Polymethylpentene (PMP), Polyphenylene oxide (PPO), Polyphenylene sulfide (PPS), Polypropylene (PP), Polystyrene (PS), Polysulfone (PSU), Polytrimethylene terephthalate (PTT), Polyvinyl acetate (PVAc), Polyvinyl alcohol (PVA), Polyvinyl chloride (PVC), Polyvinylidene chloride (PVDC), High Density Polyethylene (HDPE), Low Density Polyethylene (LDPE), Polyvinyl Chloride (PVC), Polymethylmethacrylate (PMMA), p-Polycarbonate (PC), Polyaryletherketone (PAEK) and Self-reinforced polyphenylene (SRP), Polyvinylidene chloride (PVDC), Styrene-acrylonitrile (SAN), Polychlorotrifluoroethylene (PCTFE), Nylon, Teflon, Thermoplastic polyurethanes, Phenol-formaldehyde resin, Para-aramid, Polychloroprene, Polyimide, aromatic polyester, poly-p-phenylene-2,6-benzobisoxazole (PBO), Polyethylene glycol (PEG), Polyurethane (PU), Polyvinylidene fluoride (PVDF), Ethylene methyl acrylate and combinations thereof.

The binder includes glucose, sorbitol mannitol, sorbitol, fructose, maltose, xylitol, maltitol, sucrose, lactose, starch, cellulose, microcrystalline cellulose, hydroxypropyl cellulose, ethyl cellulose, methyl cellulose, carboxy methyl cellulose, gelatin, polyvinylpyrrolidone, polyethylene glycol, poly vinyl alcohol polymethycrylate, calcium phosphate, camphor, naphthalene, wax, water and combinations thereof.

In accordance with yet another aspect of the present disclosure, a property modified composition is prepared by incorporating one or more tablets into one or more melt processable polymers to obtain a polymeric mix. The tablet is incorporated into the melt processable polymer without being heated or melted. This polymeric mix is further processed in a melt processing machine at a temperature which is higher than either the softening temperature or the melting temperature of the melt processable polymer to obtain a property modified composition.

In one embodiment of the present disclosure the tablet is mixed with the melt processable polymer before melting the melt processable polymer.

In another embodiment of the present disclosure the tablet is mixed with the melt processable polymer after melting the melt processable polymer.

The melt processable polymer in which said table is being incorporated is selected from polyethylene terephthalate, polypropylene, polyethylene, poly methyl methacrylate, polystyrene, polycarbonate, polyamide, high density polyethylene and combinations thereof.

In accordance one embodiment of the present disclosure the carrier and the melt processable polymer are selected from polyethylene terephthalate, polypropylene, polyethylene, poly methyl methacrylate, polystyrene, polycarbonate, polyamide, high density polyethylene and combinations thereof.

The melt processing machine used to prepare the property modified composition includes but is not limited to melt spinning, blow molding, extrusion blow molding, stretch blow molding, compression molding, injection molding, film casting, film extrusion, electro spinning, injection molding, compression molding, transfer molding, extrusion molding, blow molding, dip molding, rotational molding, thermoforming, laminating, expandable bead molding, foam molding, vacuum plug assist molding, pressure plug assist, matched mold, shrink fitting, shrink wrapping, die casting, rotational molding, thermoforming, blown film extrusion, over jacketing extrusion, tubing extrusion, co-extrusion, extrusion coating, and compounding.

In accordance the present disclosure the property modified composition is obtained as a molten composition or a solid composition or a molded composition.

In accordance the present disclosure the property modified composition may also be obtained in the form of chips, flaks, sheets, fibers, filaments, yarns, films or extrusions.

In accordance with still another aspect of the present disclosure an article is configured by using the property modified composition.

In one embodiment of the present disclosure the property modified composition is in the form of fibers and the article is a woven or non-woven fabric configured from said fibers.

In one embodiment the article of the present disclosure contains a core layers and a sheath layers and theses layers are prepared by using the melt processable polymer containing one or more tablets.

In another embodiment of the present disclosure the core and the sheath of the article is prepared by using same melt processable polymer containing one or more tablets.

In another embodiment of the present disclosure the core and the sheath of the article is prepared by using different melt processable polymers and one or more said melt processable polymer contains one or more tablets.

In yet another embodiment of the present disclosure the article is a bicomponent filament having the core and the sheath prepared by using same melt processable polymers containing one or more tablets.

In still another embodiment of the present disclosure the article is a bicomponent filament having the core and the sheath prepared by using different melt processable polymer and one or more said melt processable polymer contains one or more tablets.

The disclosure will now be described with the help of the following non-limiting examples. Although the example discloses the deltamethrin as a property modifying agent, person ordinarily skilled in the art can explore these examples for preparing a tablet by using other property modifying agents.

COMPARATIVE EXAMPLE 5 parts Deltamethrin powder and 95 parts Polyethylene terephthalate (PET) powder (0.80 IV) were premixed, dried at 80° C. in vacuum oven and extruded through twin screw extruder to get 5% Deltamethrin master batch. Extruder temperatures were in the range of 265° C. to 285° C. This master batch was used for making 130/36 denier partially oriented yarn (POY). Standard SD PET was used for making POY.

TABLE 1

POY details

| | 130/36-POY | 130/36-POY |
|---|---|---|
| Denier/Filament/cross section | Round | Round |
| Polymer | SDPET | SDPET |
| DeltamethrinMB LDR | 4 | 10 |

Determination of Deltamethrin in POY

POY was textured for making mosquito repellent nets. Deltamethrin Master Batch (MB) and textured yarn were tested for Deltamethrin content. Samples (0.5 g chips/1.0 g yarn) were dissolved in 10 ml Hexafluoroisopropanol (HFIP) & solution was diluted with 10 ml chloroform. The diluted solution was added to 50 ml Acetone under stirring to precipitate PET. Solution was filtered through GFC paper and filtrate was evaporated to obtain Deltamethrin residue. Residue was dissolved in carbon tetra chloride and volume was adjusted to 4 ml. Solution was filtered through GFC paper and FTIR spectra was recorded. Area of peak at 1488 cm−1 was calculated, to determine deltamethrin concentration using a calibration based on use of known amounts of deltamethrin (0.25% to 2.5% solution).

TABLE 2

Determination of Deltamethrin in POY

| Sample Identity | Deltamethrin conc. (%) expected | Deltamethrin conc. (%) measured |
|---|---|---|
| Deltamethrin (MB) | 5.0% | 4.3 (14% loss) |
| POY containing 10% Deltamethrin (MB) | 0.43% | 0.343 (20.2% loss) |
| POY containing 4% Deltamethrin MB | 0.172% | 0.13 (24.4% loss) |

There was a 14% loss in deltamethrin content during masterbatch making and 20-24% loss in Deltamethrin content during POY spinning by due to evaporation at high temp.

Example 1

5 parts deltamethrin powder & 95 parts HDPE powder (18MFI) were mixed to obtain a premix. The premix was then compacted to obtain a HDPE tablet having avg. diameter of 8 mm and avg. weight of 200 mg. Since the tablet making was carried out at temperature of 25° C., there was no loss of deltamethrin due to evaporation.

HDPE tablets were then incorporated into the melt processable polymer, HDPE at a temperature of 190° C. to obtain a property modified composition containing 1% deltamethrin. The composition was then extruded through an extruder to obtain a bi-component FDY containing a sheath of the property modified composition and a core of polyethylene terephthalate (PET)

TABLE 3

| Fully Drawn Yarn (FDY) details: | |
| --- | --- |
| Cross Section Geometry | Sheath/Core Round |
| Proportion | 25/75 (HDPE/PET) |
| Den/Fil | 50/24 |

Determination of Deltamethrin in FDY

FDY sample was refluxed at a temperature of 140° C. in 40 ml xylene for 1 hr. and was then cooled at a temperature of 25° C. and filtered by using GFC filter paper. Filtrate was diluted to 50 ml with xylene and injected in GC for determination of percentage of detamethrin in FDY. Std. Deltamethrin solution was prepared by dissolving pure deltamethrin powder in xylene.

TABLE 4

| Determination of Deltamethrin in FDY | |
| --- | --- |
| Sample Identity | Deltamethrin conc. (%) |
| FDY containing 1% Deltamethrin in a Sheath (Total Deltamethrin concentration in Bicomponent FDY = 0.25%) | 0.238 (4.8% Deltamethrin loss) |

Since the tablet preparation process was carried out at temperature of 25° C. by mechanical compression, there was no loss of Deltamethrin. During Bicomponent FDY spinning there was 4.8% loss in deltamethrin content compared to 20% to 24% loss during polyester POY.

Example 2

50 parts deltamethrin powder & 50 parts polyvinyl pyrrolidone powder (PVP K 30) were mixed to obtain a premix. The premix was then compacted to obtain a polyvinyl pyrrolidone tablet having avg. diameter of 5 mm and avg. weight of 50 mg. Since the tablet making was carried out at temperature of 25° C., there was no loss of deltamethrin due to evaporation. Polyvinyl pyrrolidone tablets were then incorporated into the melt processable polymer, polyethylene at a temperature of 190° C. to obtain a property modified composition containing 1% of detamethrin. The composition was then extruded through extruder to obtain a bi-component FDY containing a core of polyethylene terephthalate and a sheath of the property modified composition.

TABLE 3

| Fully Drawn Yarn (FDY) details: | |
| --- | --- |
| Cross Section Geometry | Sheath/Core Round |
| Proportion | 25/75 (PE/PET) |
| Den/Fil | 70/36 |

Determination of Deltamethrin in FDY

FDY sample was refluxed at a temperature of 140° C. in 40 ml xylene for 1 hr. and was then cooled at a temperature of 25° C. and filtered by using GFC filter paper. Filtrate was diluted to 50 ml with xylene and injected in GC for determination of percentage of detamethrin in FDY. Std. Deltamethrin solution was prepared by dissolving pure deltamethrin powder in xylene.

TABLE 4

| Determination of Deltamethrin in FDY | |
| --- | --- |
| Sample Identity | Deltamethrin conc. (%) |
| FDY containing 1% Deltamethrin in a Sheath (Total Deltamethrin concentration in Bicomponent FDY = 0.25%) | 0.233 (6.8% Deltamethrin loss) |

Since the tablet preparation process was carried out at temperature of 25° C. by mechanical compression, there was no loss of Deltamethrin. During Bicomponent FDY spinning there was 6.8% loss in deltamethrin content compared to 20% to 24% loss during polyester POY.

Example 3

80 parts deltamethrin powder & 20 parts ethyl cellulose powder (ethyl cellulose grade M 10) were mixed to obtain a premix. The premix was then compacted to obtain a deltamethrin tablet having avg. diameter of 4.5 mm and avg. weight of 50 mg. Since the tablet making was carried out at temperature of 25° C., there was no loss of deltamethrin due to evaporation.

Deltamethrin tablets were then incorporated into a melt processable polymer, polyethylene at a temperature of 190° C. to obtain a property modified composition containing 1% detamethrin. The composition was then extruded through extruder to obtain a bi-component FDY containing a core of polyethylene terephthalate and a sheath of the property modified composition.

TABLE 3

| Fully Drawn Yarn (FDY) details: | |
| --- | --- |
| Cross Section Geometry | Sheath/Core Round |
| Proportion | 25/75 (PE/PET) |
| Den/Fil | 70/36 |

Determination of Deltamethrin in FDY

FDY sample was refluxed at a temperature of 140° C. in 40 ml xylene for 1 hr. and was then cooled at a temperature of 25° C. and filtered by using GFC filter paper. Filtrate was diluted to 50 ml with xylene and injected in GC for determination of percentage of detamethrin in FDY. Std. Deltamethrin solution was prepared by dissolving pure deltamethrin powder in xylene.

TABLE 4

Determination of Deltamethrin in FDY

| Sample Identity | Deltamethrin conc. (%) |
|---|---|
| FDY containing 1% Deltamethrin in a Sheath (Total Deltamethrin concentration in Bicomponent FDY = 0.25%) | 0.241 (3.6% Deltamethrin loss) |

Since the tablet preparation process was carried out at temperature of 25° C. by mechanical compression, there was no loss of Deltamethrin. During Bicomponent FDY spinning there was 3.6% loss in deltamethrin content compared to 20 to 24% loss during polyester POY.

Example 4

80 parts deltamethrin powder & 20 parts poly ethylene glycol (PEG 6000) were mixed to obtain a premix. The premix was then compacted to obtain a deltamethrin PEG tablet having avg. diameter of 4.5 mm and avg. weight of 50 mg. Since the tablet making was carried out at temperature of 25° C., there was no loss of deltamethrin due to evaporation.

Deltamethrin tablets were then incorporated into the melt processable polymer, polyethylene at a temperature of 190° C. to obtain a property modified composition containing 1% detamethrin. The composition was extruded through extruder to obtain a bi-component FDY containing a core of polyethylene terephthalate and a sheath of the property modified composition.

TABLE 3

Fully Drawn Yarn (FDY) details:

| Cross Section Geometry | Sheath/Core Round |
|---|---|
| Proportion | 25/75 (PE/PET) |
| Den/Fil | 70/36 |

Determination of Deltamethrin in FDY

FDY sample was refluxed at a temperature of 140° C. in 40 ml xylene for 1 hr. and was then cooled at a temperature of 25° C. and filtered by using GFC filter paper. Filtrate was diluted to 50 ml with xylene and injected in GC for determination of percentage of detamethrin in FDY. Std. Deltamethrin solution was prepared by dissolving pure deltamethrin powder in xylene.

TABLE 4

Determination of Deltamethrin in FDY

| Sample Identity | Deltamethrin conc. (%) |
|---|---|
| FDY containing 1% Deltamethrin in a Sheath (Total Deltamethrin concentration in Bicomponent FDY = 0.25%) | 0.236 (5.6% Deltamethrin loss) |

Since the tablet preparation process was carried out at temperature of 25° C. by mechanical compression, there was no loss of Deltamethrin. During Bicomponent FDY spinning there was 5.6% loss in deltamethrin content compared to 20 to 24% loss during polyester POY.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the disclosure as it existed anywhere before the priority date of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

When the term "about" is used in describing a value or an end-point of a range, the disclosure should be understood to include the specific value or end-point referred to.

The invention claimed is:

1. A tablet adapted to modify at least one property of a melt processable polymer, said tablet comprising at least one property modifying agent and at least one processing aid having a softening temperature lower than or equal to the melt processing temperature of the melt processable polymer; wherein the amount of the processing aid is at least 0.005% with respect to the total mass of the tablet and the melt processing temperature of the melt processable polymer is higher than or equal to the initial degradation temperature of the property modifying agent.

2. The tablet as claimed in claim 1, wherein the property modifying agent is at least one selected from the group consisting of surfactants, polymerization modifiers, plasticizers, stabilizers, colorants, toners, antimicrobial agents, insect repellants, insecticides, catalysts, initiators, chain extenders, and cross linkers.

3. The tablet as claimed in claim 1, wherein the property modifying agent is at least one insect repellant selected from the group consisting of deltamethrin, permethrin, fenvalerate, cypermethrin, bifenthrin, resmethrin, sumethrin and n-octyl bicycloheptene dicarboximide.

4. The tablet as claimed in claim 1, wherein the property modifying agent is at least one synergist selected from the group consisting of piperonyl butoxide and n-octyl bicycloheptene dicarboximide.

5. The tablet as claimed in claim 1, wherein the property modifying agent is at least one insecticide and at least one synergist.

6. The tablet as claimed in claim 1, wherein the processing aid is at least one selected from the group consisting of carriers, binders, lubricants, glidants, dispersing agents and disintegrants; wherein the at least one carrier is selected from the group consisting of polymeric carriers, oligomeric carriers and monomeric carriers.

7. The tablet as claimed in claim 1, wherein the melt processable polymer is at least one polymer selected from the group consisting of polyethylene terephthalate, polypropylene, polyethylene, poly methyl methacrylate, polystyrene, polycarbonate, polyamide and high density polyethylene.

8. The tablet as claimed in claim 1, wherein the processing aid comprises at least one polymeric carrier selected from the group consisting of Acrylonitrile butadiene styrene (ABS), Cellulose acetate, Cellulose, Ethyl cellulose, Fluoroplastics (PTFE) Cyclic Olefin Copolymer (COC), Ethylene-Vinyl Acetate (EVA), acrylic/PVC alloy, Ethylene vinyl alcohol (EVOH), Liquid Crystal Polymer (LCP), Polyoxymethylene (POM or Acetal), Polyacrylates (Acrylic), Polyacrylonitrile (PAN or Acrylonitrile), Polyaryletherketone (PAEK or Ketone), Polybutylene terephthalate (PBT), Polycaprolactone (PCL), Polychlorotrifluoroethylene (PCTFE), Polyethylene terephthalate (PET), Polycyclohexylenedimethylene terephthalate (PCT), Polyhydroxyalkanoates (PHAs), Polyketone (PK) Polyester, Polyethylene (PE), Polyetheretherketone (PEEK), Polyetherketoneketone (PEKK), Polyethersulfone (PES)/Polysulfone, Chlorinated Polyethylene (CPE), Polylactic acid (PLA), Polymethylpentene (PMP), Polyphenylene oxide (PPO), Polyphenylene sulfide (PPS), Polypropylene (PP), Polystyrene (PS), Polysulfone (PSU), Polytrimethylene terephthalate (PTT), Polyvinyl acetate (PVAc), Polyvinyl alcohol (PVA), Polyvinyl chloride (PVC), Polyvinylidene chloride (PVDC), High Density Polyethylene (HDPE), Low Density Polyethylene (LDPE), Polyvinyl Chloride (PVC), Polymethylmethacrylate (PMMA), p-Polycarbonate (PC), Polyaryletherketone (PAEK) and Self-reinforced polyphenylene (SRP), Polyvinylidene chloride (PVDC), Styrene-acrylonitrile (SAN), Polychlorotrifluoroethylene (PCTFE), Thermoplastic polyurethanes, Phenol-formaldehyde resin, Para-aramid, Polychloroprene, Polyimide, aromatic polyester, poly-p-phenylene-2,6-benzobisoxazole (PBO), Polyethylene glycol (PEG), Polyurethane (PU), Polyvinylidene fluoride (PVDF) and Ethylene methyl acrylate.

9. The tablet as claimed in claim 1, wherein the processing aid consists of at least one binder selected from the group consisting of Glucose, sorbitol Mannitol, Sorbitol, Fructose, Maltose, xylitol, maltitol, sucrose, lactose, starch, cellulose, microcrystalline cellulose, hydroxypropyl cellulose (HPC); Ethyl cellulose, methyl cellulose, carboxy methyl cellulose, gelatin, polyvinylpyrrolidone (PVP), polyethylene glycol (PEG), poly vinyl alcohol (PVA), Polymethycrylate, Calcium phosphate, Camphor, naphthalene, wax and water.

10. A tablet adapted to modify at least one property of a melt processable polymer, said tablet comprising at least one property modifying agent and at least one processing aid having a softening temperature lower than or equal to the melt processing temperature of the melt processable polymer; wherein,
melt processing temperature of said melt processable polymer is higher than or equal to the initial degradation temperature of said property modifying agent;
the amount of said processing aid is at least 0.005% with respect to the total mass of said tablet; and
said processing aid is at least one oligomeric carrier selected from the group consisting of macrocyclic polycarbonates oligomer, macrocyclic polyesters oligomer, macrocyclic polyimides oligomer, macrocyclic polyetherimide oligomer, macrocyclic polyphenylene ether-polycarbonate co-oligomers, macrocyclic polyetherimide-polycarbonate co-oligomers.

11. A tablet adapted to modify at least one property of a melt processable polymer, said tablet comprising at least one property modifying agent and at least one processing aid having softening temperature lower than or equal to the melt processing temperature of the melt processable polymer; wherein,
melt processing temperature of said melt processable polymer is higher than or equal to the initial degradation temperature of said property modifying agent;
the amount of said processing aid is at least 0.005% with respect to the total mass of said tablet; and
said processing aid is at least one monomeric carrier selected from the group consisting of glucose, sorbitol, mannitol, fructose, maltose, xylitol, maltitol, sucrose, lactose, calcium phosphate, naphthalene, camphor, calcium stearate, magnesium stearate, sodium stearate, fumed silica, calcium carbonate, magnesium carbonate, carbon black, diatomaceous earth, magnesium silicate, calcium silicate, sodium silicate, alumina and wax.

* * * * *